United States Patent
Honma et al.

(10) Patent No.: US 6,320,060 B1
(45) Date of Patent: Nov. 20, 2001

(54) PROCESS FOR PRODUCING 5-HYDROXYBENZO[B] THIOPHENE-3-CARBOXYLIC ACID DERIVATIVES

(75) Inventors: Tsunetoshi Honma, Ikoma; Yoshiharu Hiramatsu, Higashiosaka, both of (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

(21) Appl. No.: 09/647,354

(22) PCT Filed: Mar. 30, 1999

(86) PCT No.: PCT/JP99/01616

§ 371 Date: Sep. 29, 2000

§ 102(e) Date: Sep. 29, 2000

(87) PCT Pub. No.: WO99/50260

PCT Pub. Date: Oct. 7, 1999

(30) Foreign Application Priority Data

Mar. 31, 1998 (JP) .................................................. 10-085819

(51) Int. Cl.[7] .................................................. C07D 333/72
(52) U.S. Cl. .................................................. 549/51
(58) Field of Search .................................................. 549/51

(56) References Cited

FOREIGN PATENT DOCUMENTS

| 97/02269 | 1/1997 | (WO) . |
| 98/25919 | 6/1998 | (WO) . |

OTHER PUBLICATIONS

Tatsuo Tsuri et al., "Bicyclo[2.2.1]heptane and 6,6–dimethyl–bicyclo[3.1.1]heptane derivatives: Orally active, potent, and selective prostagrandin D2 receptor antagonist", J. Med. Chem., (1997), 40, (22), pp. 3504–3507.

Kaoru Seno et al., "Thromboxane A2 receptor antagonists. III. Synthesis and pharmacological activity of 6,6–dimethyl–bicyclo[3.1.1]heptane derivatives with a substituted sulfonylamino group at C–2", J. Med. Chem., (1989), 37, (6), pp. 1524–1533.

M. Martin–Smith et al., "Benzo[b]thiophen derivatives. Part VI. The synthesis of 3–(2–amino–ethyl)–5–hydroxybenzo[b]thiophen and related compounds", J. Chem. Soc. C, (1967), (19), pp. 1899–1905.

Y. Makisumi et al., "Synthesis of Condensed Thiophens via [2,3] and [3,3] Sigmatropic Rearrangements of Aryl Prop–2–ynyl Sulphoxides", J.C.S., Chem. Comm., pp. 848–849, 1974.

*Primary Examiner*—Deborah C. Lambkin
*Assistant Examiner*—Andrea M. D'Souza
(74) *Attorney, Agent, or Firm*—Wenderoth, Lind & Ponack, L.L.P.

(57) ABSTRACT

Benzothiophenecarboxylic acid derivatives of the formula (I) which are useful as starting materials for producing drugs, and a process for preparing 5-hydroxybenzo[b]-thiophene-3-carboxylic acid derivatives of the formula (VI) which are specific $PGD_2$ antagonists.

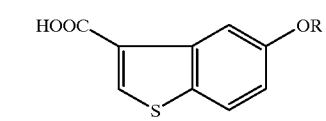

I

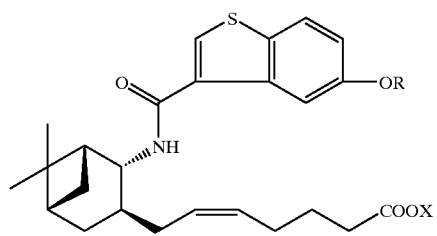

VI

8 Claims, No Drawings

PROCESS FOR PRODUCING 5-HYDROXYBENZO[B] THIOPHENE-3-CARBOXYLIC ACID DERIVATIVES

This is a 371 application of PCT/JP99/01616 filed Mar. 30, 1999.

TECHNICAL FIELD

The present invention relates to 5-hydroxybenzo[b]thiophene-3-carboxylic acid derivatives which are key starting materials for producing compounds useful in the field of pharmaceuticals.

BACKGROUND ART

5-Hydroxybenzo[b]thiophene-3-carboxylic acid derivatives of the general formula (I):

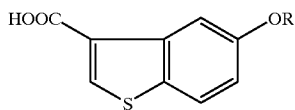

I wherein R is hydrogen or a hydroxy-protecting group are important starting materials in the synthesis of pharmacologically active compounds. For example, a compound of the formula (I) is essential in the synthesis of benzothiophenecarboxamide derivatives of the general formula (VI):

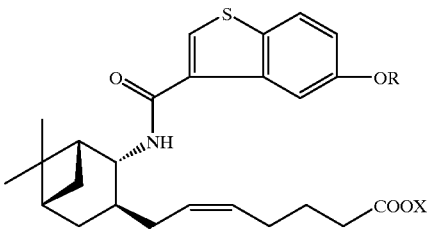

VI wherein R is as defined above and X is hydrogen or alkyl. The benzothiophenecarboxamide derivatives are specific antagonists of $PGD_2$ and known to be useful as a drug in the treatment of various diseases related to mast cell dysfunction caused by excessive production of $PGD_2$, for example, systemic mastocytosis, disorder of systemic mast cell activation, tracheal contraction, asthma, allergic rhinitis, allergic conjunctivitis, urticaria, injury due to ischemic reperfusion, inflammation, and atopic dermatis (WO97/00853, PCT/JP97/04527 (WO98/25919)). Among compounds of the formula (VI), a compound wherein OR is 5-hydroxy and X is hydrogen (hereinafter, referred to as "Compound A") has especially high antagonistic effect on $PGD_2$, showing an excellent anti-nasal occlusion activity, and is contemplated to be a promising drug for treating nasal occlusion.

DISCLOSURE OF THE INVENTION

A process for preparing the above-mentioned compound is illustrated by the following reaction scheme (WO98/25919):

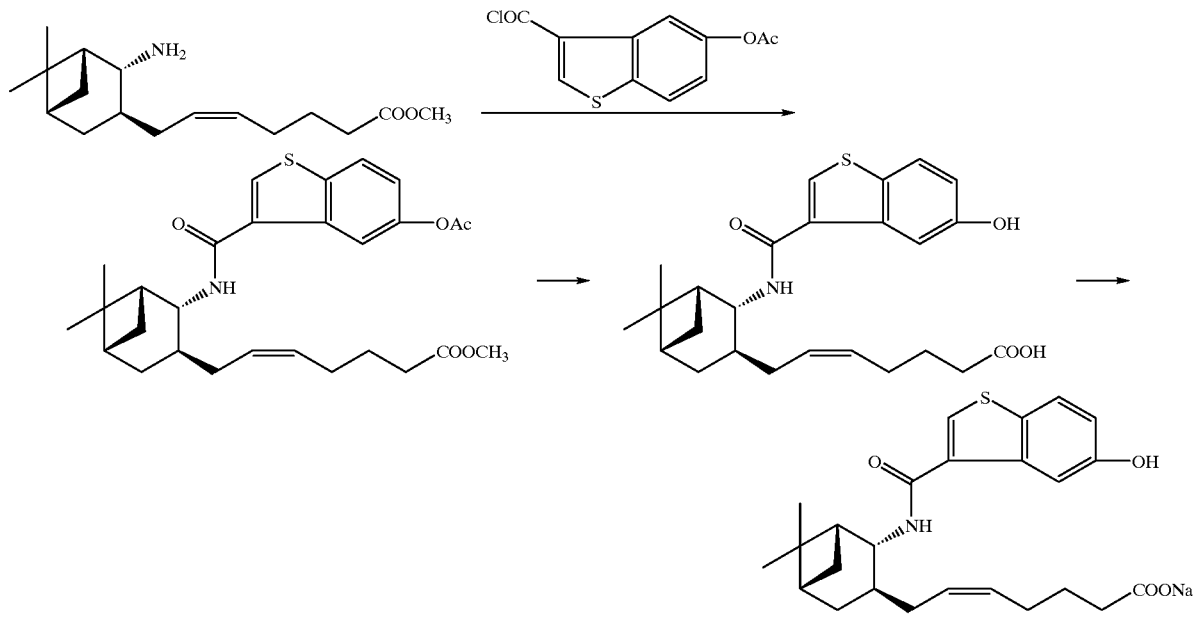

In order to clinically apply Compound A widely, it is essential to establish a process for preparing a starting material, the compound (I), which process is safe, efficient and industrially applicable.

However, it is difficult to synthesize benzothiophene derivatives having 5-hydroxyl group like the compound (I) and there have been no methods industrially applicable so far. The existing methods involve various complicated processes and are inefficient and of low yield. For example, there have been methods wherein 5-acetoxybenzo[b]thiophene is brominated to yield 3-bromo-5-acetoxybenzo[b]thiophene, which in turn is re-protected at the 5-acetoxy group with a benzyl group to yield 3-bromo-5-benzyloxybenzo[b]thiophene, which is followed by metallization with magnesium, introduction of carbon dioxide and removal of the benzyl group (J. Chem. Soc. (C). 1967, 1899–1905); or 5-bromobenzo[b]-thiophene is subjected to Friedel-Crafts reaction to yield 3-acetyl-5-bromobenzo[b]thiophene, which is followed by oxidation with sodium hypochlorite to yield 5-bromobenzo[b]thiophene-3-carboxylic acid (Nippon-Kagaku Zasshi vol. 86, No. 10, 1067–1072(1965), J. Chem. Soc. (C). 1967, 2084–2089). 5-Hydroxybenzo[b]thiophene-3-carboxylic acid or 5-acetoxybenzo[b]thiophene- 3-carboxylic acid are then synthesized starting from the reaction products above. However, the starting material such as 5-hydroxybenzo[b]-thiophene or 5-bromobenzo[b]thiophene is not commercially available and had to be synthesized from an appropriate reagent (e.g., J. Am. Chem. Soc., 57, 1611(1935), J. Heterocyclic Chem., 25, 1271(1988)) in all cases, which have made the synthetic process longer and complex.

The present invention solves the problems of the existing methods and provides a method for the preparation of the compounds of the formula (I), which method is industrially applicable, efficient and safe.

Thus, the present invention provides a process for preparing a compound of the formula (I):

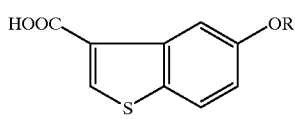

I wherein R is hydrogen or a hydroxy-protecting group, or a reactive derivative thereof comprising subjecting 4-mercaptophenol to reactions for introduction of a propargyl group and protection of hydroxyl group to yield a compound of the formula (II):

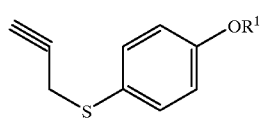

II wherein $R^1$ is a hydroxy-protecting group; oxidizing the compound (II) to yield a compound of the formula (III):

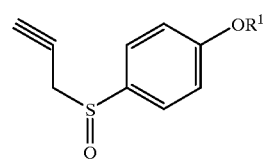

III wherein $R^1$ is a hydroxy-protecting group; subjecting the compound (III) to thermal rearrangement reaction to yield a compound of the formula (IV):

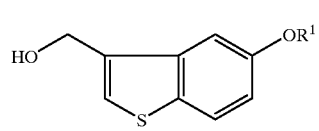

IV wherein $R^1$ is as defined above; and subjecting the compound (IV) to stepwise oxidation of hydroxymethyl group and optionally deprotection.

The present invention also provides a process for preparing a compound of the formula (I):

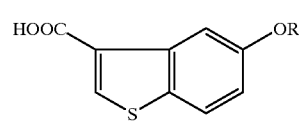

I wherein R is hydrogen or a hydroxy-protecting group or a reactive derivative thereof comprising subjecting 5-hydroxybenzo[b]thiophene to a protecting reaction to yield a compound of the formula (VII):

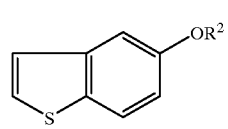

VII wherein $R^2$ is a hydroxy-protecting group; reacting the compound (VII) with acetyl halide under the conditions for Friedel-Crafts reaction to yield a compound of the formula (VIII):

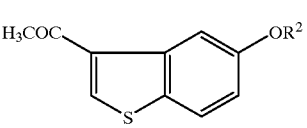

VIII wherein $R^2$ is a hydroxy-protecting group; and subjecting the compound (VIII) to oxidation of the acetyl group and optionally deprotection.

The present invention further provides a method for the preparation of the above-mentioned 5-hydroxybenzo[b]-thiophene-3-carboxylic acid derivative of the general formula (VI) by using a compound of the formula (I). Thus, the present invention provides a process for preparing a compound of the formula (VI):

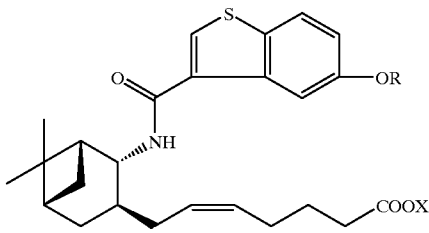

wherein R is as defined above and X is hydrogen or alkyl, and double bond represents either E- or Z-configuration, or a pharmaceutically acceptable salt thereof or a hydrate thereof, which comprises subjecting a compound of the formula (I) or a reactive derivative thereof to the following reactions:

(1) reaction with a compound of the formula (V)

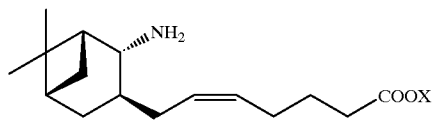

wherein X is hydrogen or alkyl; or
(2) reaction with a compound of the formula (V'):

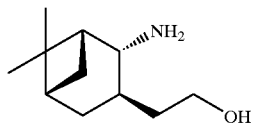

or a salt thereof followed by oxidation and reaction with an ylide under the conditions for Wittig reaction; and (3) optionally deprotection.

THE BEST EMBODIMENT FOR PRACTICING THE INVENTION

The terms used herein are defined below.

The term "hydroxy-protecting group" means alkyl, alkoxyalkyl, acyl, aralkyl, alkylsulfonyl, arylsulfonyl, alkyl-substituted silyl, alkoxycarbonyl, aryloxycarbonyl, aralkyloxycarbonyl or tetrahydropyranyl.

The term "alkyl" means $C_1$–$C_{20}$ linear or branched alkyl, particularly, methyl, ethyl, n-propyl, isopropyl, n-butyl, isobutyl, sec-butyl, tert-butyl, n-pentyl, isopentyl, neopentyl, tert-pentyl, hexyl, heptyl, octyl, nonyl, decyl, undecyl, dodecyl, tridecyl, tetradecyl, pentadecyl, hexadecyl, heptadecyl, octadecyl, nonadecyl, icosyl and the like, and $C_1$–$C_6$ alkyl is preferred.

The term "alkoxy" means $C_1$–$C_6$ linear or branched alkoxy, particularly, methoxy, ethoxy, n-propoxy, i-propoxy, n-butoxy, i-butoxy, s-butoxy, t-butoxy, n-pentyloxy, i-pentyloxy, neopentyloxy, s-pentyloxy, t-pentyloxy, n-hexyloxy, neohexyloxy, i-hexyloxy, s-hexyloxy, t-hexyloxy and the like, and $C_1$–$C_3$ alkoxy is preferred.

The term "alkoxyalkyl" means alkyl group substituted by alkoxy group, including methoxymethyl, ethoxymethyl, methoxyethoxymethyl, ethoxyethyl, methoxypropyl and the like.

The term "acyl" means $C_1$–$C_{11}$ acyl derived from aliphatic carboxylic acid or aromatic carboxylic acid. Examples of aliphatic carboxylic acid-derived acyl include acetyl, chloroacetyl, trichloroacetyl, propionyl, butyryl, valeryl and the like, and examples of aromatic carboxylic acid-derived acyl include benzoyl, p-nitrobenzoyl, p-methoxybenzoyl, p-bromobenzoyl, toluoyl, naphthoyl and the like.

The term "aryl" means phenyl, naphthyl or polycyclic aromatic hydrocarbon group and the like. In addition, aryl may be substituted by the following substituents.

Examples of substituent include alkyl such as methyl, ethyl, n-propyl, isopropyl, isobutyl, sec-butyl, tert-butyl, n-pentyl, isopentyl, neopentyl or tert-pentyl, lower alkoxy such as methoxy or ethoxy, halogen such as fluoro, chloro, bromo or iodo, nitro, hydroxy, carboxy, cyano, sulfonyl, amino, lower alkylamino such as methylamino, dimethylamino, ethylmethylamino or diethylamino, and the like. The aryl group may have one or more substituents at any possible positions. Specific examples of aryl include 2-methylphenyl, 3-methylphenyl, 4-methylphenyl, 2-ethylphenyl, 3-ethylphenyl, 4-ethylphenyl, 4-pentylphenyl, 4-carboxyphenyl, 4-acetylphenyl, 4-(N,N-dimethylamino)phenyl, 4-nitrophenyl, 4-hydroxyphenyl, 4-methoxyphenyl, 4-fluorophenyl, 4-chlorophenyl, 4-iodophenyl and the like.

The aryl group in the "aralkyl", "arylsulfonyl", "aryloxycarbonyl" or "aralkyloxycarbonyl" described below may have similar substituents as defined above.

The term "aralkyl" means an alkyl group substituted by aryl group, and includes benzyl, 4-methylbenzyl, 4-methoxybenzyl, 3,4-dimethoxybenzyl, naphthylmethyl, phenethyl, and the like.

The term "alkylsulfonyl" means a sulfonyl group substituted by alkyl group, and includes methanesulfonyl, ethanesulfonyl and the like.

The term "arylsulfonyl" means a sulfonyl group substituted by aryl group, and includes benzenesulfonyl, p-toluenesulfonyl, and the like.

The term "alkyl-substituted silyl" means mono-, di- or tri-alkyl-substituted silyl, for example, methylsilyl, dimethylsilyl, trimethylsilyl, t-butyldimethylsilyl, and the like.

The term "alkoxycarbonyl" means methoxycarbonyl, isopropoxycarbonyl, t-butoxycarbonyl, and the like.

The term "aryloxycarbonyl" means phenoxycarbonyl, and the like.

The term "aralkyloxycarbonyl" means benzyloxycarbonyl, and the like.

Although all the above-mentioned hydroxy-protecting groups are preferred as the hydroxy-protecting group shown by $R^1$, $R^2$ or R in respective formula above, aryl sulfonyl is more preferred and benzenesulfonyl is particularly preferred among them.

Examples of salts of the compound of the general formula (VI) include alkali metal salts such as lithium salt, sodium salt or potassium salt and the like, alkali earth metal salts such as calcium salt and the like, ammonium salt, salts with organic base such as tromethamine, trimethylamine, triethylamine, 2-aminobutane, tertbutylamine, diisopropylethylamine, n-butylmethylamine, n-butyldimethylamine, tri-n-butylamine, cyclohexylamine, dicyclohexylamine, N-isopropylcyclohexylamine, furfurylamine, benzylamine, methylbenzylamine, dibenzylamine, N,N-dimethylbenzylamine, 2-chlorobenzylamine, 4-methoxybenzylamine, 1-naphthalenemethylamine, diphenylbenzylamine, triphenylamine, 1-naphthylamine, 1-aminoanthracene, 2-aminoanthracene, dehydroabiethylamine, N-methylmorpholine or pyridine, or amino acid salts such as lysine salt or arginine salt.

The salts of the amino alcohol of the formula (V') include salts with organic acid such as benzoic acid, etc., and mineral acid such as hydrochloric acid, sulfuric acid, etc.

The final compound of the present invention is represented by the formula (VI) as described above, in which the double bond of the alkenylene side chain (5-heptenylene chain) may be in the E- or Z-configuration.

The method of the present invention is described below in more detail. When a substituent(s) possibly interfering the reaction is present, it can be appropriately protected and then deprotected at a desired stage. Such protection or deprotection can be accomplished by a procedure known in the art.

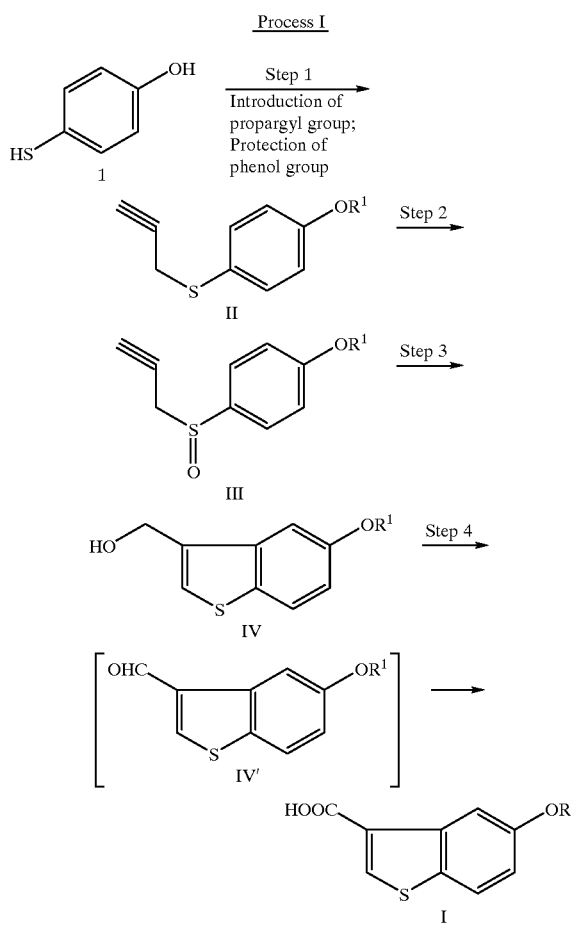

Wherein R and $R_1$ are as defined above.

[Step 1]

This step is related to the introduction of a propargyl group at the mercapto group of 4-mercaptophenol (1) and protection of hydroxyl group.

The introduction of a propargyl group is accomplished by using propargyl halide such as propargyl bromide, propargyl chloride and the like in the presence of a basic agents. The reaction can be accomplished within several tens minutes to several hours at room temperature by employing, as a basic agent, inorganic base such as potassium carbonate, sodium carbonate or the like, or an organic base such as triethylamine, pyridine, 4-dimethylaminopyridine or the like in a solvent such as acetone, ethyl acetate, tetrahydrofuran, acetonitrile, or the like.

When a strong base such as potassium hydroxide or sodium hydroxide is used, it can be also accomplished in a two-layer solvent system such as toluene-water or xylene-water.

The protection of hydroxyl group may be conducted using an ordinary hydroxy-protecting group in a conventional manner. Preferred protecting groups to be used in the present method are those which do not undergo changes during the oxidative reactions in the 2nd and 4th steps of the present Process and the 2nd step of Process IV below for the preparation of compound of the formula (VI) and also during the Wittig reaction of the 3rd step of said Process, and can be easily deprotected in the 4th step to give leaving groups which are easily separable from, for example, Compound A for purification thereof, which corresponds to a compound of the formula (VI) wherein OR is 5-hydroxy, X is hydrogen and double bond is in Z-configuration. Examples of such a hydroxy-protecting group include alkyl, alkoxyalkyl, acyl, aralkyl, alkylsulfonyl, arylsulfonyl, alkyl-substituted silyl, alkoxycarbonyl, aryloxycarbonyl, aralkyloxycarbonyl or tetrahydropyranyl.

Considering the requirements that a protecting group should survive during the Wittig reaction conducted under strong basic conditions, be easily deprotected, for example, in the 4th step for the preparation of Compound A, and be separable from Compound A, arylsulfonyl is more preferred and benzenesulfonyl is particularly preferred. Benzenesulfonyl group is relatively stable to base in anhydrous solvents and, upon deprotection, gives benzenesulfonic acid which is water-soluble and is easily separated from the final product of the formula (VI). The protection and deprotection can be carried out by a method known in the art. For example, in the case of benzenesulfonyl group, the introduction of benzenesulfonyl group is carried out in a manner similar to that for the introduction of propargyl group by using benzenesulfonyl chloride.

[Step 2]

This step is related to oxidation of the compound (II). There have been known oxidizing methods which use, for instance, aqueous hydrogen peroxide—acetic acid (J. Am, Chem. Soc., 87, 1109–1114 (1965)),aqueous hydrogen peroxide—titanium(III) chloride (Synthesis 1981, 204–206), m-chloroperbenzoic acid (Org. Synth., 64, 157–163 (1985)), or sodium metaperiodate (J. Org. Chem., 27, 282–284 (1962)). In the present step, it is preferred to use a slightly excess amount of 30% aqueous hydrogen peroxide in an alcoholic solvent such as ethanol, methanol, isopropanol or tert-butanol solution containing formic acid. The reaction is accomplished within several tens minutes to several hours under cooling or at room temperature.

[Step 3]

This step is related to the conversion of the compound (III) into the hydroxymethyl compound (IV) by thermal rearrangement reaction. The thermal rearrangement reaction in this step is carried out according to the method described in J. C, S. Chem. Comm., 1974, 848–849. Examples of preferred solvents for this reaction include dioxane, 1,2-dimethoxyethane, propyl acetate and 3-pentanone. The reaction is accomplished by refluxing in a solvent for several hours followed by adding to the resultant intermediate an acid (p-toluenesulfonic acid, methanesulfonic acid, sulfuric acid, etc.)

[Step 4]

This step is related to the oxidation of the compound (IV) to provide carboxylic acid (I). The oxidation can be carried out either directly or in a stepwise manner. Examples of oxidizing agent for converting an aromatic primary alcohol to the corresponding carboxylic acid directly include chromic acids (Synthesis. 1986, 285–288), potassium permanganate (J. Org. Chem., 18, 806–809 (1953)) and ruthenium oxides (J. C. S. Chem. Comm., 1979, 58–59)). However, these methods have disadvantages in not only the yield but also the following matters. For instance, the reaction time is long, the detoxification treatment of oxidizing agent is needed following the reaction, the reagents are unstable and/or they involve complicated operations.

On the contrary, in some cases, a stepwise oxidation wherein a primary alcohol is oxidized to an aldehyde and then to a carboxylic acid may be of advantage with regard to yield. In general, the oxidation of alcohol to aldehyde has been carried out by using an oxidizing agent of chromic acid series, for example, Jones reagents (J. Org. Chem., 40, 1664–1665 (1975)), Collins reagents (J. C. S. Chem. Comm., 1972 1126)), pyridinium chlorochromate (Tetrahedron Lett., 2647–2650 (1975)). It has been also known a method which uses manganese dioxide (Helv. Chim. Acta., 39, 858–862 (1956)) or dimethyl sulfoxide (Swern oxidation, J. Org. Chem., 43, 2480–2482 (1978)). However, these existing methods have disadvantages. For example, chromic acids are toxic to human body and must be detoxified after use. Further, the Swern oxidation using dimethyl sulfoxide-oxalyl chloride is not suited for a large scale production because it is accompanied by the generation of carbon monoxide harmful to workers and sulfurous odor and also it must be carried out at low temperature, for example, between −50° C. and −78° C.

Alcohol (IV) can be converted into aldehyde (IV') almost quantitatively by a method wherein an alcohol (IV) is oxidized with an oxidizing reagent such as halo oxoacid in the presence of 2, 2, 6, 6-tetramethylpiperidine-1-oxyl or the like (referred to as "TEMPOs") according to the description in a literature (e.g., J. Org. Chem., 52, 2559–2562 (1987)), whereby the problems of the existing methods are solved. Examples of TEMPOs usable include 2,2,6,6-tetramethylpiperidine-1-oxyl, 4-methoxy-2,2,6,6-tetramethylpiperidine-1-oxyl, 4-acetylamino-2,2,6,6-tetramethylpiperidine-1-oxyl, 4-benzoyloxy-2,2,6,6-tetramethylpiperidine-1-oxyl, and 4-cyano-2,2,6,6-tetramethylpiperidine-1-oxyl. Examples of usable halo oxoacids include sodium hypochlorite, sodium hypobromite, sodium bromite and higher bleaching powder. A solution of an oxidizing agent may be adjusted to, for example, pH 8.5 to 9.5 with a mineral acid such as sodium hydrogen carbonate, hydrogen chloride or sulfuric acid. Alternatively, a solution of an oxidizing agent may be added in the presence of sodium hydrogen carbonate. The reaction can be accomplished within several minutes to several tens minutes at temperature from ice-cooling to room temperature in a solvent such as ethyl acetate, acetonitrile or dichloromethane.

When the reaction solution containing the resultant aldehyde (IV') is acidified and sodium chlorite and aqueous hydrogen peroxide are added thereto, the aldehyde is converted into carboxylic acid under ice-cooling within several tens minutes to several hours.

If desired, the product may be further subjected to the deprotection of 5-hydroxy-protecting group and/or conversion into reactive derivatives at 3-carboxyl group. Such "reactive derivative" includes the corresponding acid halides (e.g., chloride, bromide, iodide), acid anhydrides (e.g., mixed acid anhydride with formic acid or acetic acid), activated esters (e.g., succinimide ester), and the like, and includes acylating agents generally used for the acylation of amino group. For example, to obtain acid halides, a carboxylic acid is reacted with thionyl halide (e.g., thionyl chloride), phosphorous halide (e.g., phosphorous trichloride, phosphorous pentachloride), oxalyl halide (e.g., oxalyl chloride), or the like, according to a known method (e.g., Shin-jikken Kagaku Koza, vol. 14, p. 1787 (1978); Synthesis 852–854(1986); Shin-jikken Kagaku Koza vol. 22, p. 115 (1992)).

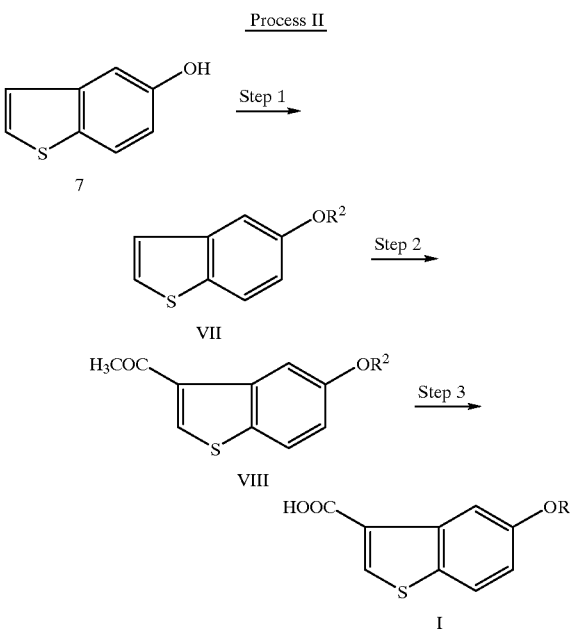

wherein R and $R^2$ are as defined above.

[Step 1]

This step is related to the protection of 5-hydroxy group of compound (7).

The compound (7) as the starting material of the present step is known in a literature (J. Am. Chem. Soc., 57, 1611–1616 (1935), Ann. Chem., 527, 83–114 (1938), J. Am. Chem. Soc., 78, 5351–5357 (1956), J. Org. Chem., 41, 1118–1124 (1976)). The hydroxyl group of this compound is protected appropriately in a manner similar to that described in the 1st step of Process I above. For example, when benzenesulfonyl group is used, the compound is added to benzenesulfonyl chloride in the presence of an inorganic base such as sodium carbonate or potassium carbonate, or an organic base such as triethylamine or tripropylamine. Example of preferred solvent includes acetone, ethyl acetate and tetrahydrofuran. The reaction is accomplished within several minutes to several hours at temperature from room temperature to the boiling point of the solvent. The compound (VII) can be also synthesized by a broadly used method, commonly known as "Schotten-Baumann reaction".

[Step 2]

This step is related to the introduction of acetyl group to the 3-position of the compound (VII) by Friedel-Crafts reaction. The introduction of acetyl group is, for example, carried out using acetyl chloride or acetyl bromide in the presence of a catalyst, for example, a Lewis acid such as aluminium chloride, ferric chloride, zinc chloride, tin chloride and boron trifluoride. Example of usable solvent includes carbon disulfide, nitrobenzene or a halogenated hydrocarbons such as methylene chloride or ethylene chloride. The reaction is in general accomplished within several hours at temperature of ice-cooling to room temperature. The 2-acetyl compound slightly produced as a by-product is easily separable by recrystallization.

[Step 3]

This step is related to the conversion of the compound (VIII) into a carboxylic acid (I) or a reactive derivative thereof through the oxidation of the acetyl group in the presence of a salt of hypohalous acid. Examples of preferred hypohalogenite include alkali metal or alkaline earth metal salts of hypohalous acids, and potassium, sodium or calcium salt of hypochlorous or hypobromous acid is especially preferred.

In an aqueous solution of such a salt, the oxidation progresses at relatively low temperature. However, dioxane or 1,2-dimethoxyethane may be used as a solvent so as to increase the solubility of the compound to be oxidized. The reaction is accomplished within several hours to several tens hours at room temperature or with heating.

Process III

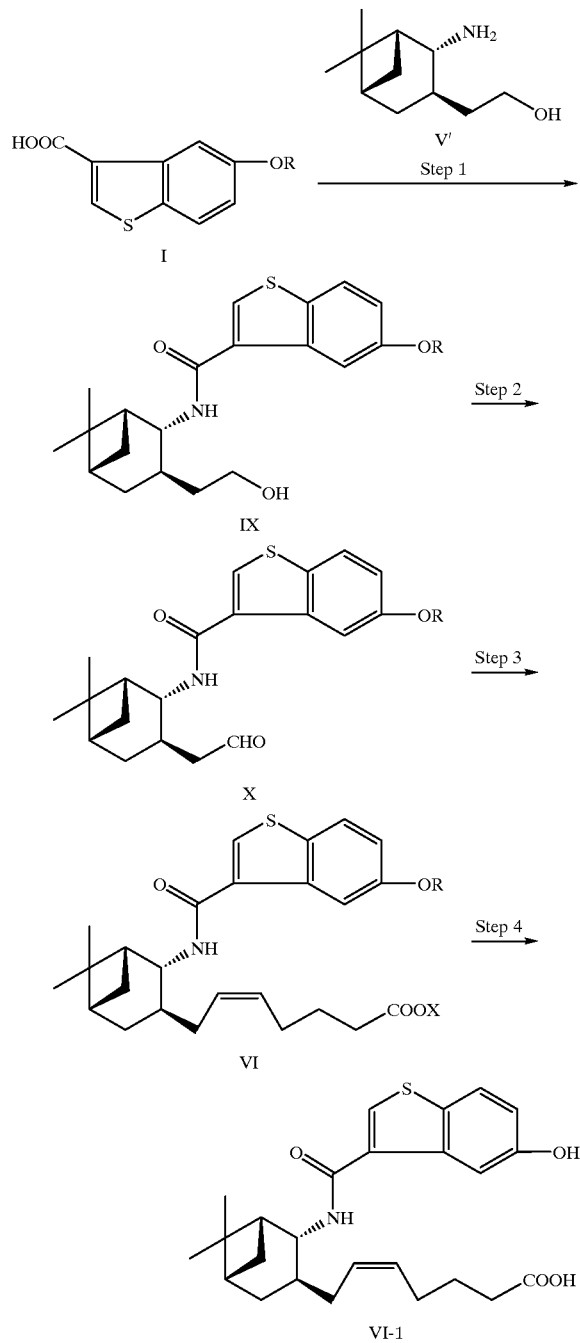

wherein R and X are as defined above and the double bond represents E- or Z-configuration.

This process is related to the synthesis of a compound of the formula (VI) by reacting a compound of the formula (I) or a reactive derivative thereof obtained in Process I or II above with a compound of the formula (V).

The compound (V) used in the present process is obtainable according to the method described in Japanese Patent Publication (KOKOKU) No. 6-23170 (23170/1994).

The reaction can be carried out under ordinary conditions for acylation of amino group. For example, when a carboxylic acid halide is used, the reaction is carried out according to a method commonly known as "Schotten-Baumann reaction". In general, carboxylic acid halide is added dropwise to an aqueous alkaline solution of amine with stirring and under cooling while removing the generating acid with alkali. Alternatively, when a carboxylic acid is used as a free acid not a reactive derivative, the reaction can be conducted conventionally in the presence of a coupling agent generally used in the coupling reaction between an amine and a carboxylic acid such as dicyclohexylcarbodiimide (DCC), 1-ethyl-3-(3-dimethylaminopropyl)carbodiimide or N,N'-carbonyldiimidazole.

wherein R and X are as defined above and the double bond represents E- or Z-configuration.

[Step 1]

This step is related to the preparation of a compound of the formula (IX) by reacting a compound of the formula (I) or a reactive derivative thereof with a compound of the formula (V') or its salt in a manner similar to that described in Process III above. The preparation of some of the compounds of the formula (V') is described in Chem. Pharm. Bull. Vol.37, No. 6 1524–1533 (1989).

[Step 2]

This step is related to the preparation of an aldehyde of the formula (X) by oxidizing a compound of the formula (IX).

The reaction can be carried out for several hours under cooling or at room temperature using an oxidizing agent selected from chromic acid series such as Jones reagents, Collins reagents, pyridinium chlorochromate, pyridinium dichromate or dimethyl sulfoxide-oxalyl chloride in a solvent such as chlorinated hydrocarbons (chloroform, dichloromethane, etc.), ethers (ethyl ether, tetrahydrofuran, etc.), acetone or benzene.

[Step 3]

This step is related to the formation of a double bond by reacting a compound of the formula (X) with an ylide (Ph$_3$P=CH(CH$_2$)$_3$COOH). The reaction for providing a double bond can be carried out in a conventional manner for Wittig reaction. The ylides used in the reaction can be synthesized, in the presence of a base, by treating a phosphonium salt which has been synthesized from triphenylphosphine and an alkyl halide having a desired alkyl group to be condensed, for example, 5-bromopentanoic acid. Examples of a base include dimsyl sodium, dimsyl potassium, sodium hydride, n-butyl lithium, potassium t-butoxide and lithium diisopropylamide. The reaction is accomplished within several hours at room temperature in a solvent such as ether, tetrahydrofuran, n-hexane, 1,2-dimethoxyethane or dimethyl sulfoxide.

[Step 4]

In this step, a compound (VI) wherein R is hydroxy-protecting group is optionally deprotected to give compound (VI-1). The reaction can be carried out in a conventional manner using a catalyst such as hydrochloric acid, sulfuric acid, sodium hydroxide, potassium hydroxide or barium hydroxide, or the like. The reaction is accomplished within several tens minutes to several hours with heating in a solvent such as methanol-water, ethanol-water, acetone-water, acetonitrile-water, or the like, preferably dimethyl sulfoxide-water.

The following Examples are provided to further illustrate the present invention in more detail and should not be interpreted in any way as to limit the scope thereof. The abbreviations used in the Examples have the following meanings:

Ph: phenyl
Ac: acetyl
TEMPO: 2,2,6,6-tetramethylpiperidine-1-oxyl

EXAMPLE 1

(1) Step 1:

4-(2-Propyn-1-ylthio)phenyl benzenesulfonate (2)

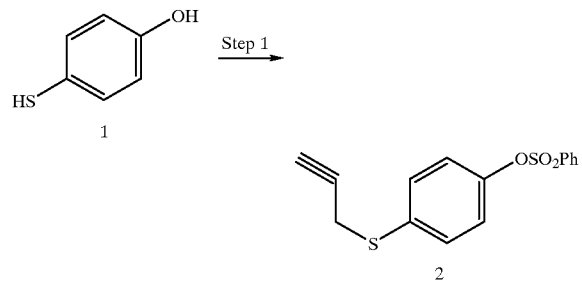

4-Mercaptophenol (1) (37.85 g, 300 mmol) and propargyl bromide (42.82 g, 360 mmol) were dissolved in ethyl acetate (757 ml). To the solution was added dropwise triethylamine (42.5 g, 420 mmol) over 25 minutes with stirring and under ice-cooling. After stirring for another 1.5 hours at the same temperature, triethylamine (42.5 g, 420 mmol) was added in one portion, and benzenesulfonyl chloride (63.58 g, 360 mmol) was added dropwise over 20 minutes. After keeping 1 hour at the same temperature, the cooling bath was removed and the mixture was stirred for 30 minutes at room temperature and partitioned into two layers by adding ice-water (500 ml) and 2N hydrochloric acid (110 ml). The aqueous layer was extracted with ethyl acetate (200 ml). The combined organic layer was washed with water, dried over anhydrous magnesium sulfate, and then the solvent was distilled off under reduced pressure to provide 100.04 g of the title compound (2) as oil. Crude yield: 109%.

IR (CHCl$_3$); 3306, 3071, 3031, 3019, 3009, 1585, 1486, 1449, 1378 cm$^{-1}$;

$^1$H NMR δ (CDCl$_3$), 300 MHz; 2.23 (1H, t, J=2.7 Hz), 3.56 (2H, d, J=2.7 Hz), 6.94 and 7.34 (each 2H, each d, J=8.7 Hz), 7.51–7.56 (2H, m), 7.68 (1H, m), 7.82–7.85 (2H, m).

(2) Step 2:

4-(2-Propyn-1-ylthio)phenyl benzenesulfonate (3)

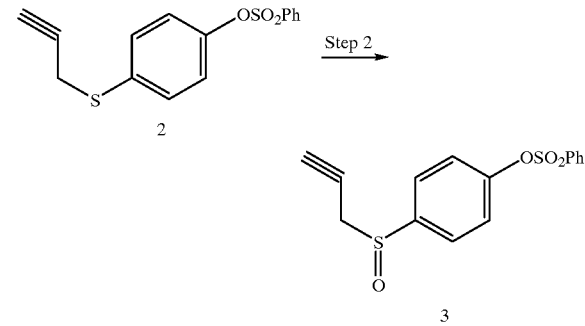

The compound (2) (60.8 g, 183 mmol) prepared in step (1) above was dissolved in formic acid (30.4 ml) and methanol (122 ml), and 31% aqueous hydrogen peroxide (26.29 g, 240 mmol) was then added. After 3.5 hours, ice-water (240 ml) was added and the mixture was extracted with ethyl acetate (2×300 ml). The combined organic layer was washed with 5% aqueous sodium carbonate and water, dried over anhydrous magnesium sulfate and the solvent was then distilled off under reduced pressure to provide 65.47 g of the title compound (3) as oil. Crude yield: 117%.

IR (CHCl$_3$); 3305, 3066, 3032, 3012, 1586, 1486, 1449, 1382 cm$^{-1}$ $^1$H NMR δ (CDCl$_3$), 300 MHz; 2.34 (1H, t, J=3.9 Hz), 3.58 and 3.68 (each 1H, each dd, J=3.9 and 23.7 Hz), 7.18 and 7.67 (each 2H, each d, J=9.9 Hz), 7.51–7.59 (2H, m), 7.66 (1H, m), 7.82–7.87 (2H, m)

(3) Step 3:

5-Benzenesulfonyloxy-3-hydroxymethylbenzo[b]thiophene (4)

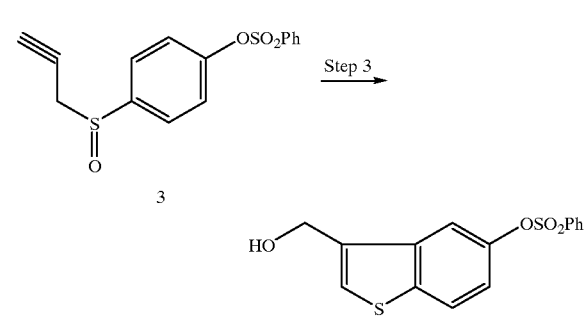

The compound (3) (65.47 g, 183 mmol) obtained in above (2) was dissolved in 1,2-dimethoxyethane (1.6L) and the solution was refluxed for 4 hours. To the solution were added water (64 ml) and p-toluenesulfonic acid monohydrate (19.2 g, 100 mmol) and refluxing was continued for 2 hours. The reaction mixture was concentrated under reduced pressure. After water (200 ml) was added to the resulting oil, the mixture was extracted with ethyl acetate (300 ml). The organic layer was washed with aqueous sodium hydrogen carbonate and water, dried over anhydrous magnesium sulfate and then the solvent was distilled off under reduced pressure to provide 60.18 g of the title compound (4) as oil. Crude yield: 103%.

IR (CHCl$_3$); 3609, 3067, 3033, 3013, 2935, 2878, 1589, 1566, 1449, 1435, 1376 cm$^{-1}$; $^1$H NMR δ (CDCl$_3$), 300 MHz; 4.78 (2H, d, J=0.9 Hz), 6.98 (1H, dd, J=2.4 and 8.7 Hz), 7.26 (1H, s), 7.43–7.45 (2H, m), 7.50–7.55 (2H, m), 7.66 (1H, m), 7.73 (1H, d, J=8.7 Hz ), 7.83–7.86 (2H, m)

(4) Step 4:

5-Benzenesulfonyloxybenzo[b]thiophene-3-carboxylic acid (6)

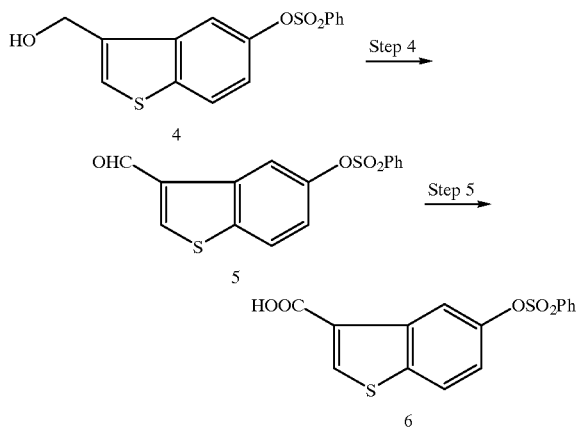

The compound (4) (51.26 g, 155 mmol) prepared in above (3) was dissolved in acetonitrile (1.54L), and TEMPO (2, 2, 6, 6-tetramethylpiperidine-1-oxyl, 250 mg, 0.01 eq.) was added thereto. To the mixture was added dropwise 0.81 N aqueous sodium hypochlorite, which had been prepared by diluting 1.63 N aqueous sodium hypochlorite (150 ml) with water (75 ml), adjusting pH 8.6 with 1 N sulfuric acid, and adjusting the total volume to 300 ml, over 15 minutes, while maintaining the inner temperature between –1° C. and 8° C. After stirring for 25 minutes at this temperature, 1 N aqueous sodium sulfite (32 ml) was added. Subsequently, 79% sodium chlorite (27.48 g, 240 mmol) and 31% aqueous hydrogen peroxide (23.26 g, 212 mmol) were added under ice-cooling. The cooling bath was removed and the mixture was stirred for 2 hours. The reaction was diluted with water (1.5L), adjusted to pH 3 with 1 N hydrochloric acid and the deposited crystals were filtered, and washed twice with water (200 ml), acetonitrile (50 ml) to provide 32.4 g of crude crystals. The crude crystals (32.4 g) were suspended in acetonitrile (224 ml), refluxed for 15 minutes and cooled on ice. The crystals were filtered and washed with acetonitrile (65 ml) to provide 26.79 g of the title compound (6). Yield: 51.7%, mp 202–203° C.

IR (Nujol): 3102, 2925, 2854, 2744, 2640, 2577, 1672, 1599, 1558, 1500, 1460, 1451 cm$^{-1}$; NMR δ (CDCl$_3$), 300 MHz; 7.16 (1H, dd, J=2.7 and 9.0 Hz), 7.55–7.61 (2H, m), 7.73 (1H, m), 7.81 (1H, d, J=9.0 Hz), 7.90–7.94 (2H, m), 8.16 (1H, d, J=2.7 Hz), 8.60 (1H, s); Elemental Analyses for C$_{15}$H$_{10}$O$_5$S$_2$; Calculated (%): C, 53.88; H, 3.01; S, 19.18; Found (%): C, 53.73; H, 3.24; S, 19.09.

EXAMPLE 2

(1) Step 1:

5-Benzenesulfonyloxybenzo[b]thiophene (8)

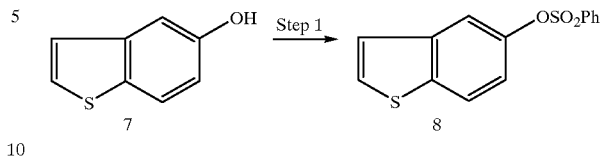

The compound (7) [J. Am. Chem. Soc., 57, 1611–1616 (1935) ; Ann. Chem., 52, 83–114 (1938), J. Am. Chem. Soc., 78, 5351–5357 (1956) ; J. Org. Chem., 41, 1118–1124 (1976)] (1.36 g, 9.05 mmol) and triethylamine (1.89 ml, 13.6 mmol) were dissolved in tetrahydrofuran (10 ml). To the solution was added dropwise a solution of benzenesulfonyl chloride (1.92 g, 10.9 mmol) in tetrahydrofuran (3 ml). After being stirred for 2 hours, the reaction mixture was diluted with water and extracted with toluene. The organic layer was washed with water, dried over anhydrous magnesium sulfate and then the solvent was distilled off under reduced pressure. The residue was chromatographed over silica gel (5:1 hexane:ethyl acetate) and then recrystallized from hexane containing small amount of ethyl acetate to provide 2.28 g of the title compound (8). Yield: 86.8%, mp 80–81° C.

IR (Nujol): 1599, 1579, 1564, 1497, 1448, 1440, 1415, 1352 cm$^{-1}$; $^1$H NMR δ (CDCl$_3$); 300 MHz; 6.92 (1H, dd, J=2.4 and 8.7 Hz), 7.26 (1H, dd, J=0.9 and 5.4 Hz), 7.47 (1H, d, J=2.4 Hz), 7.51 (1H, d, J=5.4 Hz), 7.52–7.55 (2H, m), 7.67 (1H, m), 7.74 (1H, d, J=8.7 Hz), 7.83–7.87 (2H, m) Elemental Analyses for C$_{14}$H$_{10}$O$_3$S$_2$; Calculated (%): C, 57.91; H, 3.47; S, 22.09; Found (%): C, 57.72; H, 3.45; S, 21.98.

(2) Step 2:

3-Acetyl-5-benzenesulfonyloxy-benzo[b]thiophene (9)

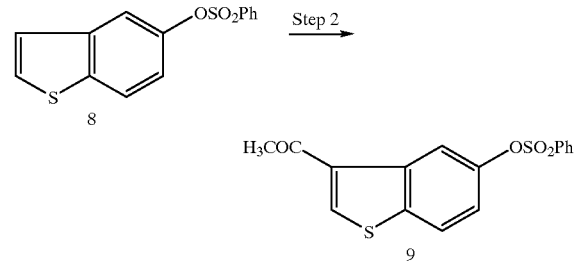

Powdered aluminum chloride (1.34 g, 10 mmol) was suspended in dichloromethane (10 ml). To the suspension was added dropwise acetyl chloride (1.02 ml, 14.3 mmol) over 5 minutes with stirring and under ice-cooling. Subsequently, a solution of the compound (8) (2.075 g, 7.2 mmol) prepared above in dichloromethane (6 ml) was added dropwise over 15 minutes. After being stirred for 2 hours at the same temperature and then for 2.5 hours at room temperature, the solution was poured into ice-water and extracted with dichloromethane. The organic layer was washed with water, dried over anhydrous magnesium sulfate and then the solvent was distilled off under reduced pressure. The resulting residue was recrystallized from ethyl acetate (3 ml) and hexane (3 ml) to provide 2.01 g of the title compound (9). Yield: 84.4% mp 129–130° C.

IR (Nujol): 3094, 1672, 1619, 1596, 1556, 1494, 1450, 1437, 1428, 1369 cm$^{-1}$; $^1$H NMR δ (CDCl$_3$); 300 MHz; 2.58 (3H, s), 7.22 (1H, ddd, J=0.6, 2.4 and 9.0 Hz), 7.52–7.58 (2H, m), 7.69 (1H, m), 7.79 (1H, d, J=9.0 Hz), 7.87–7.91

(2H, m), 8.27 (1H, dd, J=0.6 and 2.4 Hz), 8.31 (1H, s); Elemental Analyses for $C_{16}H_{12}O_4S_2$; Calculated (%): C, 57.82; H, 3.64; S, 19.29; Found (%): C, 57.62; H, 3.71; S, 19.23.

(3) Step 3:

5-Benzenesulfonyloxybenzo[b]thiophene-3-carboxylic acid (6)

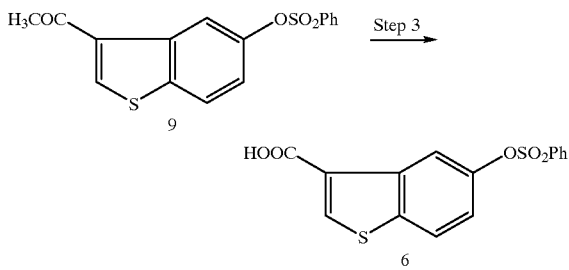

The compound (9) (6.65 g, 20 mmol) prepared in above (2) was dissolved in dioxane (50 ml), and 10% sodium hypochlorite (46.2 ml) was added over 20 minutes with stirring while maintaining the temperature at 10–12° C. After 7 hours, the reaction mixture was diluted with ice-water (80 ml) and acidified with conc. hydrochloric acid (5.2 ml). The deposited crystals were filtered, washed with water, dried to provide 5.84 g of crude crystals. The 5.84 g of the crude crystals were recrystallized from methanol (66 ml) and water (16 ml) to provide 5.51 g of the title compound (6). Yield: 82.4%. mp 203–204° C.

This compound is identical to the compound (6) prepared in Example 1.

Reference Example 1

5-Benzenesulfonyloxybenzo[b]thiophene-3-carbonyl chloride (10)

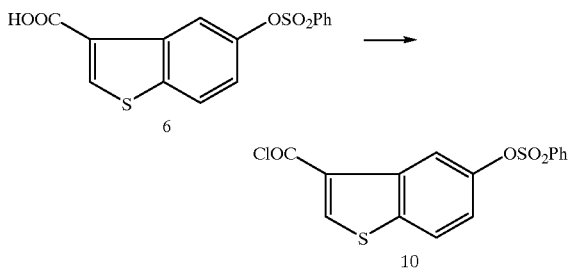

5-Benzenesulfonyloxybenzo[b]thiophene-3-carboxylic acid (6) (5.582 g, 16.7 mmol) prepared in Examples above was refluxed for 1.5 hours with dimethylformamide (1 drop), thionyl chloride (3.57 ml, 50 mmol) and toluene (22 ml), and the solvent was removed under reduced pressure to provide 5.89 g of the title compound (10).

Reference Example 2

(1) Step 1:

5-Hydroxybenzo[b]thiophene-3-carboxylic acid (11)

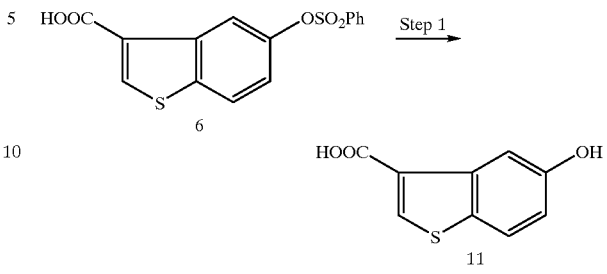

5-Benzenesulfonyloxybenzo[b]thiophene-3-carboxylic acid (6) (100 mg, 0.3 mmol) prepared in Examples above was dissolved in 1 N sodium hydroxide (1.2 ml) and heated at 40° C. for 8 hours with stirring. To the reaction solution was added 1 N hydrochloric acid (1.2 ml), and the deposited crystals were filtered, washed with water and dried to provide 58 mg of the title compound (11). Yield: 96.6% mp 262–263° C.

This compound (11) is identical to 5-hydroxybenzo[b]thiophene-3-carboxylic acid described in M. Martin-Smith et al. J. Chem. Soc (C), 1899–1905 (1967).

(2) Step 2:

5-Acetoxybenzo[b]thiophene-3-carboxylic acid (12)

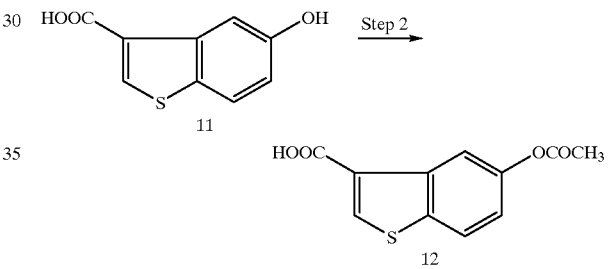

5-Hydroxybenzo[b]thiophene-3-carboxylic acid (11) (1,140 mg) prepared in above (1) was dissolved in acetic anhydride (2 ml), pyridine (4 ml). After 3 hours, water was added and the mixture was continuously stirred under ice-cooling for 1.5 hours. The deposited crystals were filtered, washed with water and dried to provide 1,349 mg of the title compound (12). Yield: 97.3% mp 239–240° C.

$^1$H NMR δ (CDCl$_3$), 300 MHz; 2.37 (H, s), 7.20 (1H, dd, J=2.4 and 8.7 Hz), 7.87 (1H, d, J=8.7 Hz), 8.34 (1H, d, J=2.4 Hz), 8.57 (1H, s).

(3) Step 3:

5-Acetoxybenzo[b]thiophene-3-carbonyl chloride (13)

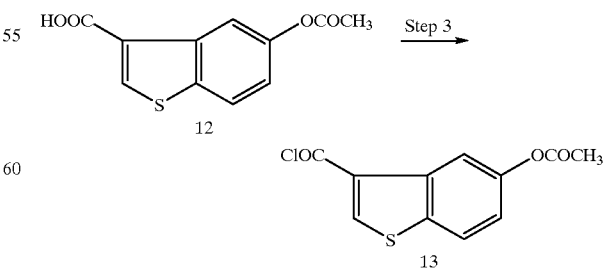

5-Acetoxybenzo[b]thiophene-3-carboxylic acid (12) (1,349 mg) prepared above was refluxed for 1.5 hours with dimethylformamide (1 drop), thionyl chloride (1.22 ml) and toluene (25 ml). The solvent was removed under reduced pressure to provide 1,454 mg of the title compound (13).

EXAMPLE 3

(5Z)-7-[(1R,2R,3S,5S)-2-(5-Hydroxybenzo[b]thiophen-3-ylcarbonylamino)-10-norpinan-3-yl]-5-heptenoic acid (17)

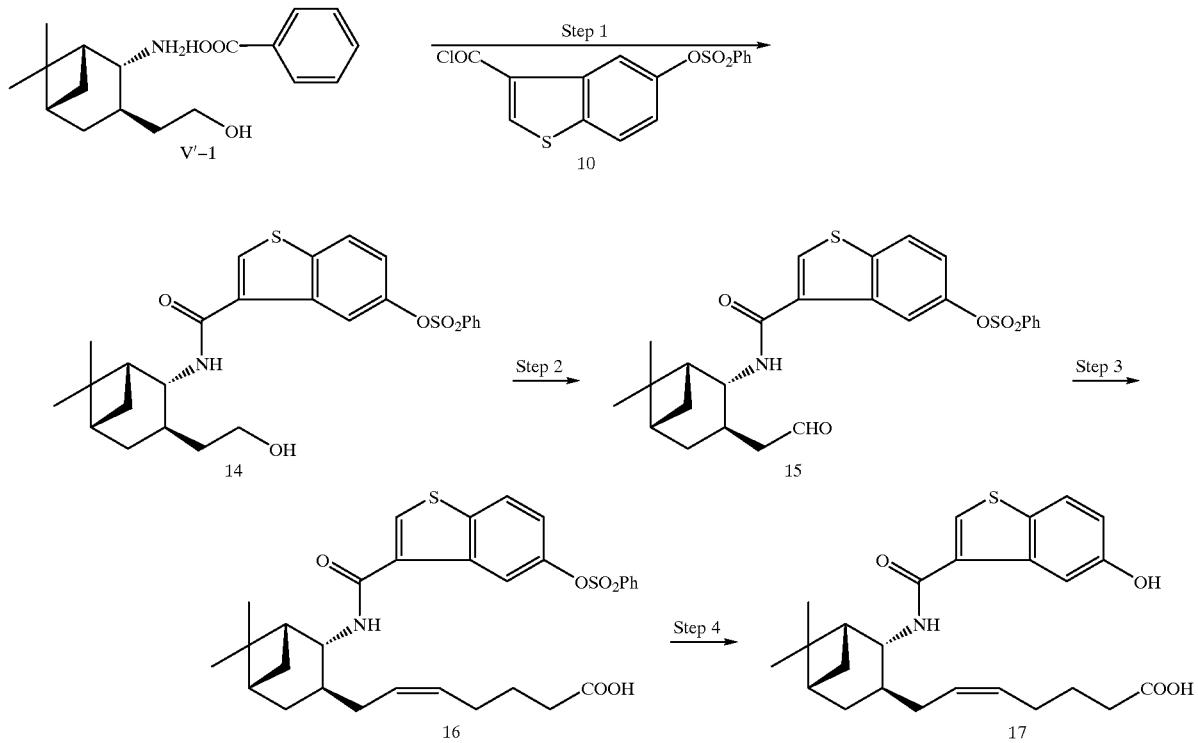

(1) Step 1: Preparation of [3-[(1R,2R,3R,5S)-3-(2-Hydroxyethyl)-10-norpinan-2-yl]carbamoylbenzo[b]thiophen-5-yl]benzenesulfonate (14)

Benzoic acid salt of (+)-2-[(1R,2R,3R,5S)-2-Amino-10-norpinan-3-yl]ethanol (described in Chem. Pharm. Bull. Vol.37, No. 6 1524–1533(1989) (V'-1)) (5.1 g, 16.7 mmol) was suspended in water (10 ml). To the suspension was added 1 N hydrochloric acid (17 ml) and deposited benzoic acid was removed by extracting with ethyl acetate. The organic layer was washed with water (10 ml). To the combined aqueous layer was added 4 N sodium hydroxide (9.2 ml, 36.8 mmol) under ice-cooling. A solution of 5-benzenesulfonyloxybenzo[b]thiophene-3-carbonyl chloride (10) (5.89 g, 16.7 mmol) in tetrahydrofuran (36 ml) was then added dropwise over 15 minutes with stirring. After stirring for 1 hour at the same temperature, 1 N hydrochloric acid (4 ml) was added and the mixture was extracted with ethyl acetate. The organic layer was washed with water, dried over anhydrous magnesium sulfate and then the solvent was distilled off under reduced pressure to provide 8.00 g (95.6%) of the title compound (14) as colorless amorphous.

$^1$H NMR δ (CDCl$_3$), 300 MHz; 0.96 (1H, d, J=9.9 Hz), 1.12 and 1.26 (each 3H, each s), 1.50–2.42 (9H, m), 3.69–3.82 (2H, m), 4.30 (1H, m), 6.21 (1H, d, J=8.1 Hz), 7.06 (1H, dd, J=2.4 and 8.7 Hz), 7.51–7.56 (2H, m), 7.67 (1H, m), 7.73 (1H, d, J=8.7 Hz), 7.85–7.88 (2H, m), 7.88 (1H, s), 8.06 (1H, d, J=2.4 Hz).

$[\alpha]_D^{25}$+35.7° (c=1.00%, CH$_3$OH).

(2) Step 2: Preparation of [3-[(1R,2R,3R,5S)-3-Formylmethyl-10-norpinan-2-yl]carbamoylbenzo[b]thiophen-5-yl]benzenesulfonate (15)

To dimethyl sulfoxide (3.16 ml, 44.5 mmol) dissolved in dimethoxyethane (50 ml) was added oxalyl chloride (1.91 ml, 21.9 mmol) under cooling at −60° C.−−65° C. A solution of compound (14) (7.352 g, 14.7 mmol) in 1,2-dimethoxyethane (58 ml) was added dropwise at the same temperature. After stirring the mixture at −55° C.−−60° C. for 30 minutes, triethylamine (6.1 ml) was added and, 30 minutes later, the cooling bath was removed to allow the mixture to warm up to room temperature. The reaction mixture was diluted with water (100 ml) and extracted with toluene. The organic layer was washed with water, dried over anhydrous magnesium sulfate and then the solvent was distilled off under reduced pressure. The resulting residue was purified by chromatography on silica gel (hexane:ethyl acetate=5:5–4:6) to provide 7.32 g (100%) of the title compound (15) as colorless amorphous.

IR (CHCl$_3$); 3443, 3093, 3066, 3030, 3016, 2925, 2871, 2828, 2729, 1720, 1655, 1599, 1558, 1513, 1377 cm$^{-1}$; $^1$H NMR δ (CDCl$_3$), 300 MHz; 0.97 (1H, d, J=10.2 Hz), 1.17 and 1.28 (each 3H, each s), 1.46 (1H, m), 2.03 (1H, m), 2.22 (1H, m), 2.36–2.60(3H, m), 2.69 (1H, ddd, J=1.2, 8.7 and 17.4 Hz), 3.14 (1H, dd, J=4.5 and 17.4 Hz), 4.28 (1H, m), 6.18 (1H, d, J=8.1 Hz), 7.09 (1H, dd, J=2.4 and 8.7 Hz), 7.50–7.55 (2H, m), 7.67 (1H, m), 7.75 (1H, d, J=8.7 Hz), 7.85–7.89 (2H, m), 7.89 (1H ,s), 8.03 (1H, d, J=2.4 Hz), 9.80 (1H, d, J=1.2 Hz) $[\alpha]_D^{23}$+31.8° (c=1.00%, CH$_3$OH).

(3) Step 3: Preparation of (5Z)-7-[(1R,2R,3S,5S)-2-(5-Benzenesulfonyloxybenzo[b]thiophen-3-ylcarbonylamino)-10-norpinan-3-yl]-5-heptenoic acid (16)

4-Carboxybutyltriphenylphosphonium bromide (12.17 g, 27.5 mmol) and potassium t-butoxide (7.19 g, 64.1 mmol) were suspended in tetrahydrofuran (64 ml) and stirred for 1 hour under ice-cooling. To the reaction mixture was added over 15 minutes a solution of the compound (15) (9.11 g, 18.3 mmol) prepared in above (2) in tetrahydrofuran (27 ml) and the mixture was continuously stirred for 2 hours at the same temperature. The reaction mixture was diluted with water (80 ml) and washed with toluene (2×105 ml). After adjusting the aqueous layer to pH 8.1 with 5 N hydrochloric acid (4.8 ml), anhydrous calcium chloride (8.1 g, 73 mmol) dissolved in water (16 ml) was added, and the mixture was extracted with ethyl acetate (2×100 ml). Water (100 ml) was added to the organic layer, and the aqueous layer was adjusted to below pH 2 with 5 N hydrochloric acid and extracted with ethyl acetate. The organic layer was washed with water, dried over anhydrous magnesium sulfate and then the solvent was distilled off under reduced pressure to provide 11.06 g of the compound (16). The compound (16) was used in the next reaction without further purification.

(4) Step 4: Preparation of (5Z)-7-[(1R,2R,3S,5S)-2-(5-Hydroxybenzo[b]thiophen-3-ylcarbonylamino)-10-norpinan-3-yl]-5-heptenoic acid (17) (Compound A))

The compound (16) (11.06 g, 18.3 mmol) prepared in above (3) was dissolved in dimethyl sulfoxide (22 ml). After adding 4 N sodium hydroxide (27.5 ml), the mixture was heated at 55° C. for 2 hours with stirring. The reaction mixture was diluted with water (130 ml) and washed with toluene (2×65 ml). The aqueous layer was acidified with 5 N hydrochloric acid and extracted with ethyl acetate. The organic layer was washed with water, dried over anhydrous magnesium sulfate, and the solvent was distilled off under reduced pressure to provide 8.26 g of the crude objective compound which was then dissolved in methanol (40 ml) and water (16 ml). The solution was seeded and gradually cooled with stirring. The deposited crystals were filtered and washed with water:methanol (2:5) to provide 6.35 g of the objective compound. Yield: 78.6%. The crystals were dissolved in methanol (40 ml). To the solution was added water (12 ml) over 7 minutes with stirring. The mixture was seeded and continuously stirred for 1 hour at 25° C. After adding water (7 ml) over 40 minutes, the mixture was stirred for 1.5 hours at 25° C. The deposited crystals were filtered and washed with water:methanol (3:5) (8 ml) to provide 6.14 g of the objective compound (17) which was almost colorless. Yield: 76.0%, mp 145–146° C.

IR (Nujol); 3313, 3096, 3059, 3001, 1717, 1627, 1603, 1548, 1469, 1440 cm$^{-1}$; $^1$H NMR δ (CDCl$_3$), 300 MHz; 1.02 (1H, d, J=10.2 Hz), 1.12 and 1.24 (each 3H, each s), 1.56–2.55(14H, m), 4.29 (1H, m), 5.32–5.51 (2H, m), 6.20 (1H, d, J=9.3 Hz), 7.01 (1H, dd, J=2.4 and 9.0 Hz), 7.66 (1H, d, J=9.0 Hz), 7.69 (1H ,s), 8.03 (1H, d, J=2.4 Hz); $[α]_D^{24}$+ 50.7° (c=1.01, CH$_3$OH); Elemental Analyses for C$_{25}$H$_{31}$NO$_4$S; Calculated (%): C, 68.00; H, 7.08; N, 3.17; S, 7.26; Found (%): C, 67.84; H, 7.08; N, 3.24; S, 7.31.

What is claimed is:

1. A process for producing a compound of the formula (I):

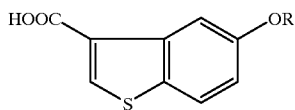

wherein R is hydrogen or a hydroxy-protecting group, or a reactive derivative thereof, which comprises introducing a propargyl group into 4-mercaptophenol, and protecting the hydroxyl group of the 4-mercaptophenol, to yield a compound of the formula (II):

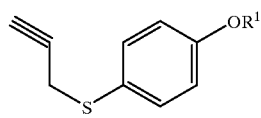

wherein $R^1$ is a hydroxy-protecting group, oxidizing the compound (II) to yield a compound of the formula (III):

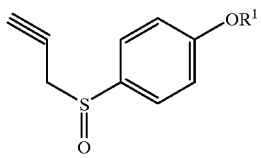

wherein $R^1$ is a hydroxy-protecting group; subjecting the compound (III) to a thermal rearrangement reaction to yield a compound of the formula (IV):

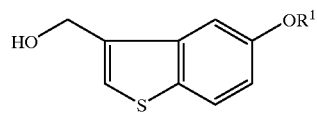

wherein $R^1$ is as defined above; and subjecting the compound (IV) to stepwise oxidation of the hydroxymethyl group and optionally deprotection.

2. The process of claim 1, wherein the hydroxy-protecting group represented by $R^1$ is alkyl, alkoxyalkyl, acyl, aralkyl, alkylsulfonyl, arylsulfonyl, alkyl-substituted silyl, alkoxycarbonyl, aryloxycarbonyl, aralkyloxycarbonyl or tetrahydropyranyl.

3. The process of claim 1, wherein the hydroxy-protecting group represented by $R^1$ is arylsulfonyl.

4. A compound of the formula (I):

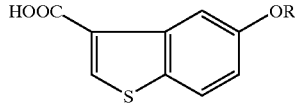

wherein R is arylsulfonyl or a reactive derivative thereof.

5. A compound of the formula (I):

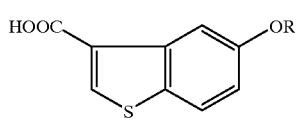

wherein R is benzenesulfonyl or a reactive derivative thereof.

6. The process for producing a compound of the formula (I) according to claim 1, wherein the reactive derivative is an acid halide, activated ester or acylating agent of said compound.

7. The compound of the formula (I) according to claim 4, wherein the reactive derivative is an acid halide, activated ester or acylating agent of said compound.

8. The compound of the formula (I) according to claim 5, wherein the reactive derivative is an acid halide, activated ester or acylating agent of said compound.

* * * * *